(12) United States Patent
Henne et al.

(10) Patent No.: US 11,490,946 B2
(45) Date of Patent: Nov. 8, 2022

(54) VAPOR ABLATION HANDPIECE

(71) Applicant: Uptake Medical Technology Inc., Seattle, WA (US)

(72) Inventors: Erik Henne, Seattle, WA (US); Joshua Pieter Kroon, Seattle, WA (US); Joseph Jin Hyo Lee, Seattle, WA (US); Robert Barry, Kirkland, WA (US)

(73) Assignee: Uptake Medical Technology Inc., Seattle, WA (US)

( * ) Notice: Subject to any disclaimer, the term of this patent is extended or adjusted under 35 U.S.C. 154(b) by 855 days.

(21) Appl. No.: 16/203,541

(22) Filed: Nov. 28, 2018

(65) Prior Publication Data

US 2019/0175245 A1 Jun. 13, 2019

Related U.S. Application Data

(60) Provisional application No. 62/598,138, filed on Dec. 13, 2017.

(51) Int. Cl.
*A61B 18/04* (2006.01)
*A61B 18/00* (2006.01)

(52) U.S. Cl.
CPC .... *A61B 18/04* (2013.01); *A61B 2018/00541* (2013.01); *A61B 2018/00577* (2013.01); *A61B 2018/00815* (2013.01); *A61B 2018/00916* (2013.01); *A61B 2018/044* (2013.01); *A61B 2018/048* (2013.01); *A61M 2205/36* (2013.01)

(58) Field of Classification Search
CPC .............. A61B 18/04; A61B 2018/048; A61B 2018/00815; A61B 2018/044; A61B 2018/00916; A61B 2018/00577; A61B 2018/00541; A61M 2205/36
USPC .......................................................... 606/27
See application file for complete search history.

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| AU | 721086 B2 | 6/2000 |
| EP | 1003582 B1 | 2/2003 |

(Continued)

OTHER PUBLICATIONS

Zinn, Stanley, Coil design and fabrication: basic design and modifications, 1988 (Year: 1988).*

(Continued)

*Primary Examiner* — Linda C Dvorak
*Assistant Examiner* — Christine A Dedoulis
(74) *Attorney, Agent, or Firm* — Richard Batt

(57) ABSTRACT

A vapor ablation handpiece for assisting a physician perform vapor ablation with a vapor ablation catheter includes a vapor generating element arranged in a coil shape. A mandrel seated in the body of the handpiece affixes the vapor generating element in the coiled arrangement. A voltage difference is supplied across the length of the vapor generating element when activated, causing the vapor generating element to heat liquid therein converting the liquid to vapor. The heated condensable vapor is delivered to a target tissue through the catheter.

20 Claims, 6 Drawing Sheets

(56) References Cited

U.S. PATENT DOCUMENTS

| | | | |
|---|---|---|---|
| 3,331,246 A * | 7/1967 | Clark | G01M 9/02 |
| | | | 374/148 |
| 3,507,283 A | 4/1970 | Thomas | |
| 3,880,168 A | 4/1975 | Berman | |
| 4,026,285 A | 5/1977 | Jackson | |
| 4,713,060 A | 12/1987 | Riuli | |
| 4,773,410 A | 9/1988 | Blackmer et al. | |
| 4,793,352 A | 12/1988 | Eichenlaub | |
| 4,915,113 A | 4/1990 | Holman | |
| 4,950,266 A | 8/1990 | Sinofsky | |
| 5,006,119 A | 4/1991 | Acker et al. | |
| 5,011,566 A | 4/1991 | Hoffman | |
| 5,084,043 A | 1/1992 | Hertzmann et al. | |
| 5,112,328 A | 5/1992 | Taboada et al. | |
| 5,158,536 A | 10/1992 | Michael et al. | |
| 5,263,951 A | 11/1993 | Spears et al. | |
| 5,331,947 A | 7/1994 | Shturman | |
| 5,334,190 A | 8/1994 | Seiler | |
| 5,348,551 A | 9/1994 | Spears et al. | |
| 5,352,512 A | 10/1994 | Hoffman | |
| 5,424,620 A | 6/1995 | Cheon et al. | |
| 5,425,414 A | 6/1995 | Bradley, Jr. et al. | |
| 5,462,521 A | 10/1995 | Brucker et al. | |
| 5,500,012 A | 3/1996 | Brucker et al. | |
| 5,503,638 A | 4/1996 | Cooper et al. | |
| 5,524,620 A | 6/1996 | Rosenschein | |
| 5,529,076 A | 6/1996 | Schachar | |
| 5,542,928 A * | 8/1996 | Evans | A61B 18/082 |
| | | | 604/113 |
| 5,549,628 A | 8/1996 | Cooper et al. | |
| 5,562,608 A | 10/1996 | Michael et al. | |
| 5,575,803 A | 11/1996 | Cooper et al. | |
| 5,591,157 A | 1/1997 | Hennings et al. | |
| 5,620,440 A | 4/1997 | Heckele et al. | |
| 5,695,507 A | 12/1997 | Auth et al. | |
| 5,735,811 A | 4/1998 | Brisken | |
| 5,752,965 A | 5/1998 | Francis et al. | |
| 5,755,753 A | 5/1998 | Knowlton | |
| 5,782,914 A | 7/1998 | Schankereli | |
| 5,800,482 A | 9/1998 | Pomeranz et al. | |
| 5,824,703 A | 10/1998 | Clark, Jr. | |
| 5,827,268 A | 10/1998 | Laufer | |
| 5,913,856 A | 6/1999 | Chia et al. | |
| 5,957,919 A | 9/1999 | Laufer | |
| 5,964,752 A | 10/1999 | Stone | |
| 5,972,026 A | 10/1999 | Laufer et al. | |
| 5,986,662 A | 11/1999 | Argiro et al. | |
| 5,989,445 A | 11/1999 | Wise et al. | |
| 6,032,077 A | 2/2000 | Pomeranz | |
| 6,053,909 A | 4/2000 | Shadduck | |
| 6,059,011 A | 5/2000 | Giolo | |
| 6,083,255 A | 7/2000 | Laufer et al. | |
| 6,099,251 A | 8/2000 | Lafleur | |
| 6,102,037 A | 8/2000 | Koch | |
| 6,113,722 A | 9/2000 | Hoffman et al. | |
| 6,130,671 A | 10/2000 | Argiro | |
| 6,131,570 A | 10/2000 | Schuster et al. | |
| 6,139,571 A | 10/2000 | Fuller et al. | |
| 6,156,036 A | 12/2000 | Sussman et al. | |
| 6,162,232 A | 12/2000 | Shadduck | |
| 6,179,805 B1 | 1/2001 | Sussman et al. | |
| 6,194,066 B1 | 2/2001 | Hoffman | |
| 6,200,333 B1 | 3/2001 | Laufer | |
| 6,210,404 B1 | 4/2001 | Shadduck | |
| 6,219,059 B1 | 4/2001 | Argiro | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,299,633 B1 | 10/2001 | Laufer | |
| 6,300,150 B1 | 10/2001 | Venkatasubramanian | |
| 6,312,474 B1 | 11/2001 | Francis et al. | |
| 6,327,505 B1 | 12/2001 | Medhkour et al. | |
| 6,394,949 B1 | 5/2002 | Crowley et al. | |
| 6,398,759 B1 | 6/2002 | Sussman et al. | |
| 6,398,775 B1 | 6/2002 | Perkins et al. | |
| 6,409,723 B1 | 6/2002 | Edwards | |
| 6,411,852 B1 | 6/2002 | Danek et al. | |
| 6,458,231 B1 | 10/2002 | Wapner et al. | |
| 6,468,313 B1 | 10/2002 | Claeson et al. | |
| D466,213 S | 11/2002 | Snitkin et al. | |
| 6,488,673 B1 | 12/2002 | Laufer et al. | |
| 6,493,589 B1 | 12/2002 | Medhkour et al. | |
| 6,508,816 B2 | 1/2003 | Shadduck | |
| 6,527,761 B1 | 3/2003 | Soltesz et al. | |
| 6,575,929 B2 | 6/2003 | Sussman et al. | |
| 6,579,270 B2 | 6/2003 | Sussman et al. | |
| 6,585,639 B1 | 7/2003 | Kotmel et al. | |
| 6,588,613 B1 | 7/2003 | Pechenik et al. | |
| 6,589,201 B1 | 7/2003 | Sussman et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,629,951 B2 | 10/2003 | Laufer et al. | |
| 6,652,594 B2 | 11/2003 | Francis et al. | |
| 6,653,525 B2 | 11/2003 | Ingenito et al. | |
| 6,669,694 B2 | 12/2003 | Shadduck | |
| 6,676,628 B2 | 1/2004 | Sussman et al. | |
| 6,679,264 B1 | 1/2004 | Deem et al. | |
| 6,682,520 B2 | 1/2004 | Ingenito | |
| 6,692,494 B1 | 2/2004 | Cooper et al. | |
| 6,712,812 B2 | 3/2004 | Roschak et al. | |
| 6,719,738 B2 | 4/2004 | Mehier | |
| 6,755,794 B2 | 6/2004 | Soukup | |
| 6,770,070 B1 | 8/2004 | Balbierz | |
| 6,776,765 B2 | 8/2004 | Soukup et al. | |
| 6,860,847 B2 | 3/2005 | Alferness et al. | |
| 6,885,888 B2 | 4/2005 | Rezai | |
| 6,901,927 B2 | 6/2005 | Deem et al. | |
| 6,904,909 B2 | 6/2005 | Deem et al. | |
| 6,907,881 B2 | 6/2005 | Suki et al. | |
| 6,911,028 B2 | 6/2005 | Shadduck | |
| 6,986,769 B2 | 1/2006 | Nelson et al. | |
| 6,997,189 B2 | 2/2006 | Biggs et al. | |
| 7,022,088 B2 | 4/2006 | Keast et al. | |
| 7,027,869 B2 | 4/2006 | Danek et al. | |
| 7,031,504 B1 | 4/2006 | Argiro et al. | |
| 7,083,612 B2 | 8/2006 | Littrup et al. | |
| 7,128,748 B2 | 10/2006 | Mooradian et al. | |
| 7,136,064 B2 | 11/2006 | Zuiderveld | |
| 7,144,402 B2 | 12/2006 | Kuester et al. | |
| 7,144,588 B2 | 12/2006 | Nicholas et al. | |
| 7,175,644 B2 | 2/2007 | Cooper et al. | |
| 7,192,400 B2 | 3/2007 | Campbell et al. | |
| 7,198,635 B2 | 4/2007 | Danaek et al. | |
| 7,233,820 B2 | 6/2007 | Gilboa | |
| 7,235,070 B2 | 6/2007 | Vanney | |
| 7,335,195 B2 | 2/2008 | Mehier | |
| 7,347,859 B2 | 3/2008 | Garabedian et al. | |
| D574,492 S | 8/2008 | Løwenstein | |
| 7,412,977 B2 | 8/2008 | Fields et al. | |
| 7,422,563 B2 | 9/2008 | Roschak et al. | |
| 7,422,584 B2 | 9/2008 | Loomas et al. | |
| 7,425,212 B1 | 9/2008 | Danek et al. | |
| D580,549 S | 11/2008 | Schwartz et al. | |
| 7,462,162 B2 | 12/2008 | Phan et al. | |
| D604,842 S | 11/2009 | Bisleri | |
| 7,628,789 B2 | 12/2009 | Soltesz et al. | |
| D610,679 S | 2/2010 | Nakagawa et al. | |
| 7,708,712 B2 | 5/2010 | Phan et al. | |
| 7,740,017 B2 | 6/2010 | Danek et al. | |
| 7,778,704 B2 | 8/2010 | Rezai et al. | |
| 7,815,590 B2 | 10/2010 | Cooper | |
| 7,819,908 B2 | 10/2010 | Ingenito | |
| D627,066 S | 11/2010 | Romero | |
| D632,787 S | 2/2011 | Tenger et al. | |
| 7,906,124 B2 | 3/2011 | Laufer et al. | |
| 7,913,698 B2 | 3/2011 | Barry et al. | |
| D640,789 S | 6/2011 | Peine et al. | |
| D641,871 S | 7/2011 | Tenger et al. | |
| 7,985,187 B2 | 7/2011 | Wibowo et al. | |
| 7,993,323 B2 | 8/2011 | Barry et al. | |
| 8,002,740 B2 | 8/2011 | Willink et al. | |
| D646,384 S | 10/2011 | Gauthier et al. | |
| D646,385 S | 10/2011 | Gauthier et al. | |

(56) References Cited

U.S. PATENT DOCUMENTS

| | | | |
|---|---|---|---|
| D650,073 S | 12/2011 | Pedersen et al. |
| D652,920 S | 1/2012 | Sherwood et al. |
| 8,088,127 B2 | 1/2012 | Mayse et al. |
| 8,172,827 B2 | 5/2012 | Deem et al. |
| 8,187,269 B2 | 5/2012 | Shadduck et al. |
| 8,251,070 B2 | 8/2012 | Danek et al. |
| 8,292,882 B2 | 10/2012 | Danek et al. |
| 8,322,335 B2 | 12/2012 | Barry et al. |
| 8,568,141 B2 | 10/2013 | Tanaka et al. |
| 8,585,645 B2 | 11/2013 | Barry et al. |
| 8,626,495 B2 | 1/2014 | Boldt et al. |
| 8,734,380 B2 | 5/2014 | Barry et al. |
| 8,858,549 B2 | 10/2014 | Shadduck et al. |
| D717,431 S | 11/2014 | Cardinale et al. |
| 8,900,223 B2 | 12/2014 | Shadduck |
| 9,050,076 B2 | 6/2015 | Barry et al. |
| 9,113,858 B2 | 8/2015 | Barry et al. |
| D774,034 S | 12/2016 | Kheradpir et al. |
| D776,874 S | 1/2017 | Kling et al. |
| D777,321 S | 1/2017 | Nakagami et al. |
| D777,914 S | 1/2017 | Wapler et al. |
| 9,561,068 B2 | 2/2017 | Sharma et al. |
| D785,185 S | 4/2017 | Yang et al. |
| D812,744 S | 3/2018 | Robinson et al. |
| D813,400 S | 3/2018 | Bechtel et al. |
| 10,842,557 B2* | 11/2020 | Sharma .................. A61B 17/24 |
| 2002/0077516 A1 | 6/2002 | Flanigan |
| 2002/0111386 A1 | 8/2002 | Michael et al. |
| 2002/0112723 A1 | 8/2002 | Schuster et al. |
| 2002/0177846 A1 | 11/2002 | Mulier et al. |
| 2003/0055415 A1* | 3/2003 | Yu ......................... A61B 18/02 606/21 |
| 2003/0099279 A1 | 5/2003 | Venkatasubramanian et al. |
| 2003/0144658 A1* | 7/2003 | Schwartz ........... A61B 18/1492 606/41 |
| 2003/0164408 A1* | 9/2003 | Schmon ................ B05B 12/008 239/291 |
| 2003/0181917 A1 | 9/2003 | Gertner |
| 2003/0181922 A1 | 9/2003 | Alferness |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0055606 A1 | 3/2004 | Hendricksen et al. |
| 2004/0068306 A1 | 4/2004 | Shadduck |
| 2004/0199226 A1 | 10/2004 | Shadduck |
| 2004/0200484 A1 | 10/2004 | Springmeyer |
| 2004/0244803 A1 | 12/2004 | Tanaka |
| 2005/0016530 A1 | 1/2005 | Mccutcheon et al. |
| 2005/0066974 A1 | 3/2005 | Fields et al. |
| 2005/0166925 A1 | 8/2005 | Wilson et al. |
| 2005/0171396 A1 | 8/2005 | Pankratov et al. |
| 2005/0171582 A1 | 8/2005 | Matlock |
| 2005/0203483 A1 | 9/2005 | Perkins et al. |
| 2005/0215991 A1 | 9/2005 | Altman et al. |
| 2005/0222485 A1 | 10/2005 | Shaw et al. |
| 2006/0004400 A1 | 1/2006 | Mcgurk et al. |
| 2006/0047291 A1 | 3/2006 | Barry |
| 2006/0100619 A1 | 5/2006 | Mcclurken et al. |
| 2006/0130830 A1 | 6/2006 | Barry |
| 2006/0135955 A1 | 6/2006 | Shadduck |
| 2006/0162731 A1 | 7/2006 | Wondka et al. |
| 2006/0200076 A1 | 9/2006 | Gonzalez et al. |
| 2006/0224154 A1 | 10/2006 | Shadduck et al. |
| 2007/0032785 A1 | 2/2007 | Diederich et al. |
| 2007/0036417 A1 | 2/2007 | Argiro et al. |
| 2007/0068530 A1 | 3/2007 | Pacey |
| 2007/0091087 A1 | 4/2007 | Zuiderveld |
| 2007/0092864 A1 | 4/2007 | Reinhardt et al. |
| 2007/0102011 A1 | 5/2007 | Danek et al. |
| 2007/0106292 A1 | 5/2007 | Kaplan et al. |
| 2007/0109299 A1 | 5/2007 | Peterson |
| 2007/0112349 A1 | 5/2007 | Danek et al. |
| 2007/0118184 A1 | 5/2007 | Danek et al. |
| 2007/0137646 A1 | 6/2007 | Weinstein et al. |
| 2007/0293853 A1 | 12/2007 | Truckai et al. |
| 2008/0033493 A1 | 2/2008 | Deckman et al. |
| 2008/0132826 A1 | 6/2008 | Shadduck et al. |
| 2008/0281267 A1 | 11/2008 | Mehier |
| 2009/0018538 A1 | 1/2009 | Webster et al. |
| 2009/0043301 A1 | 2/2009 | Jarrard et al. |
| 2009/0138001 A1 | 5/2009 | Barry et al. |
| 2009/0149846 A1 | 6/2009 | Hoey et al. |
| 2009/0192508 A1 | 7/2009 | Laufer et al. |
| 2009/0216220 A1 | 8/2009 | Hoey et al. |
| 2009/0306640 A1 | 12/2009 | Glaze et al. |
| 2009/0312753 A1 | 12/2009 | Shadduck |
| 2010/0094270 A1 | 4/2010 | Sharma |
| 2010/0204688 A1 | 8/2010 | Hoey et al. |
| 2010/0256714 A1 | 10/2010 | Springmeyer |
| 2010/0262133 A1 | 10/2010 | Hoey et al. |
| 2011/0077628 A1 | 3/2011 | Hoey et al. |
| 2011/0160648 A1 | 6/2011 | Hoey |
| 2011/0270031 A1 | 11/2011 | Frazier et al. |
| 2011/0301587 A1 | 12/2011 | Deem et al. |
| 2012/0016363 A1 | 1/2012 | Mayse et al. |
| 2012/0016364 A1 | 1/2012 | Mayse et al. |
| 2013/0006231 A1 | 1/2013 | Sharma et al. |
| 2013/0035751 A1* | 2/2013 | Shalev .................... A61B 5/01 623/1.12 |
| 2013/0116683 A1* | 5/2013 | Shadduck ........ A61B 17/32037 606/41 |
| 2013/0267939 A1 | 10/2013 | Barry et al. |
| 2014/0005594 A1* | 1/2014 | Humbert ................ A61B 18/04 604/26 |
| 2014/0200568 A1* | 7/2014 | Sharma ................ A61B 5/1076 606/27 |
| 2014/0324037 A1 | 10/2014 | Hoey et al. |
| 2015/0090575 A1* | 4/2015 | Wang .................... A61B 34/76 200/505 |
| 2015/0094607 A1 | 4/2015 | Barry et al. |
| 2015/0230852 A1 | 8/2015 | Barry et al. |
| 2016/0151103 A1 | 6/2016 | Henne et al. |
| 2016/0220296 A1* | 8/2016 | Hastings ................ A61B 18/04 |
| 2016/0220297 A1 | 8/2016 | Kroon et al. |
| 2017/0164999 A1 | 6/2017 | Hettel |
| 2017/0231676 A1 | 8/2017 | Sharma et al. |

FOREIGN PATENT DOCUMENTS

| | | |
|---|---|---|
| EP | 1143864 B1 | 2/2004 |
| EP | 1173103 B1 | 10/2005 |
| EP | 1326549 B1 | 12/2005 |
| EP | 1326548 B1 | 1/2006 |
| EP | 1485033 B1 | 8/2009 |
| WO | 0011927 A2 | 3/2000 |
| WO | 0102042 A1 | 1/2001 |
| WO | 02069821 A1 | 9/2002 |
| WO | 03028540 A2 | 4/2003 |
| WO | 03070302 A1 | 8/2003 |
| WO | 03086498 A2 | 10/2003 |
| WO | 2005025635 A2 | 3/2005 |
| WO | 2005102175 A2 | 11/2005 |
| WO | 2006003665 A2 | 1/2006 |
| WO | 2006052940 A2 | 5/2006 |
| WO | 2006053308 A2 | 5/2006 |
| WO | 2006053309 A2 | 5/2006 |
| WO | 2006080015 A2 | 8/2006 |
| WO | 2006116198 A2 | 11/2006 |
| WO | 2008051706 A2 | 5/2008 |
| WO | 2009009236 A1 | 1/2009 |
| WO | 2009009398 A1 | 1/2009 |
| WO | 2009015278 A1 | 1/2009 |
| WO | 2009137819 A1 | 11/2009 |
| WO | 2010042461 A1 | 4/2010 |
| WO | 2011006020 A1 | 1/2011 |
| WO | 2011056684 A2 | 5/2011 |

(56) References Cited

FOREIGN PATENT DOCUMENTS

| WO | 2011060201 A1 | 5/2011 |
|---|---|---|
| WO | 2011127216 A2 | 10/2011 |

OTHER PUBLICATIONS

Becker, et al.; Lung volumes before and after lung volume reduction surgery; Am J Respir Crit Care Med; vol. 157; pp. 1593-1599; (1998) Oct. 28, 1997.

Blacker, G. F.; Vaporization of the uterus; J. of Obstetrics and Gynaecology; vol. 33; pp. 488-511; (year of publication is sufficiently earlier than the effective U.S. filing.

Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.

clinical trials.gov,; Study of the AeriSeal System for HyPerinflation Reduction in Emphysema; 4 pages; Nov. 5, 2014; retrieved from the internet (http://clinicaltrials.gov/show/N.

Coda, et al., "Effects of pulmonary reventilation on gas exchange after cryolytic disobstruction of endobronchial tumors," Minerva Medical, vol. 72, pp. 1627-1631, Jun. 1981.

Delaunois; Anatomy and physiology of collateral respiratory pathways; Eur. Respir, J,; 2(9); pp. 893-904; Oct. 1989.

Eyal et al.; The acute effect of pulmonary burns on lung mechanics and gas exchange in the rabbit; Br J. Anaesth.; vol. 47; pp. 546-552; (year of publication is sufficiently.

Ferlay et al.; GLOBOCAN 2008 v1.2, Cancer Incidence and Mortality Worldwide: IARC CancerBase No. 10 [internet]; 16 pages; retrieved from the internet (http://www.iarc.fr/en/me.

Fishman et al., A randomized trial comparing lung-volume reduction surgery with medical therapy for severe emphysema, N Engl J Med, vol. 348, No. 21, pp. 2059-2073, May 22, 2003.

Goldberg et al.; Radiofrequency tissue ablation in the rabbit lung: Efficacy and complications; Acad. Radiol.; vol. 2; pp. 776-784; Sep. 1995.

Herth et al., Efficacy predictors of lung volume reduction with zephyr valves in a european cohort, Eur.Respir. J.: 39(6) pp. 1334-1342, Jun. 2012.

Homasson, et al., "Bronchoscopic cryotherapy for airway strictures caused by tumors," Chest, vol. 90, No. 2, Aug. 1986.

Kinsella, et al., "Quantitation of emphysema by computer tomography useing a densitymask program and correlation with pulmonary function tests," Chest 97(2), Feb. 1990.

Logra, R., "Mechanism of changes in the respiratory and cardio-vascular reflexes from the lungs associated with intrapulmonary steam burns," Eng.Trans from Byulleten Experimental not Bioiogii I Meditsiny: vol. 6, No. 6, Jun. 1966.

Marasso, et al., "Cryosurgery in bronchoscopic treatment of tracheobrachial stenosis," Chest, vol. 103, No. 2, Feb. 1993.

Marasso, et al., "Radiofrequency resection of bronchial tumors in combination with cryotherapy; evaluation of a new technique," Thorax, vol. 53, 1998.

Mathur, et al., "Fiberoptic bronchoscopic cryotherapy in the management of trachebronchial obstruction," Chest, vol. 110, No. 3, Sep. 1996.

Morice, et al., "Endobrinchial argon plasma coagulation for treatment of hemotysis and neoplastic airway obstruction," Chest, vol. 119, No. 3, Mar. 2001.

Moritz, et al., "The effects of inhaled heat on the air passage and lungs," American J. of Pathology, vol. XXI, 1944.

Moulding, et al., "Preliminary studies for achieving transcervical oviduct occlusion by hot water or low pressure steam," Advances in Planned Parenthood, vol. 12 No. 2, 1977.

National Lung Screening Trial Research Team, "Reduced Lung Cancer mortality with low dose computed tomographic screening," N. Eng. J.Med, 365(5), Aug. 2011.

Pracht, Adam, "VIDA takes new approach," Iowa City Press Citizen, Sep. 12, 2005.

Quin, J., "Use of neodymium yttrium aluminum garnet laser in long term palliation of airway obstruction," Connecticut Medicine, vol. 59, No. 7, Jul. 1995.

Sciurba et al., "A randomized study of endobronchial valves for advanced emphysema," N.Eng J. Med, 363(13), Sep. 2010.

Shah, et al., "Collateral ventilation and selection of techniques for bronchscopic lung volume reduction," Thorax, 67(4), Apr. 2012.

Slebos, et al., "Bronchoscopic lung volume reduction coil treatment of patients with sever heterogeneous emphysema," Chest, 142(3), Sep. 2012.

Sutedja, et al, "Bronchoscopic treatment of lung tumors," Elsevier, Lung Cancer, Jul. 11, 1994.

Tschirren, "Interthoracic Airway Trees: Segmentation and Airway Morphology Analysis from Low Dose CT Scans," IEEE Transactions on Medical Imaging, vol. 24, No. 12, 2005.

Van De Velde, "Vapo-cauterization of the uterus," Amer.J.Med, Sci vol. CXVII, 1899.

Vorre, et al., "Morphology of tracheal scar after resection with C02 laser and high-frequency cutting loop," Acta Otolaryngol (Stockh), vol. 107, 1989.

\* cited by examiner

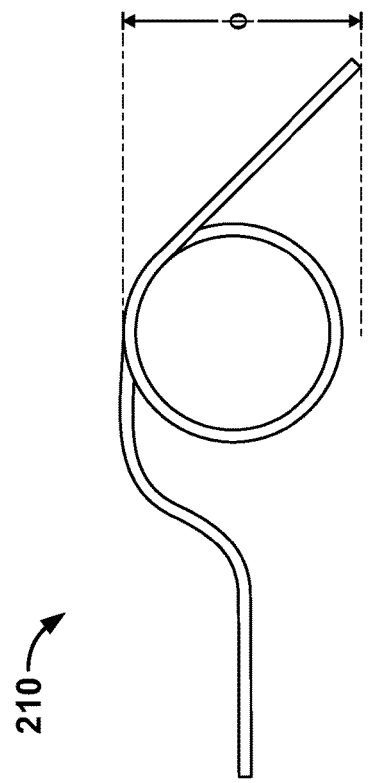
FIG. 6A
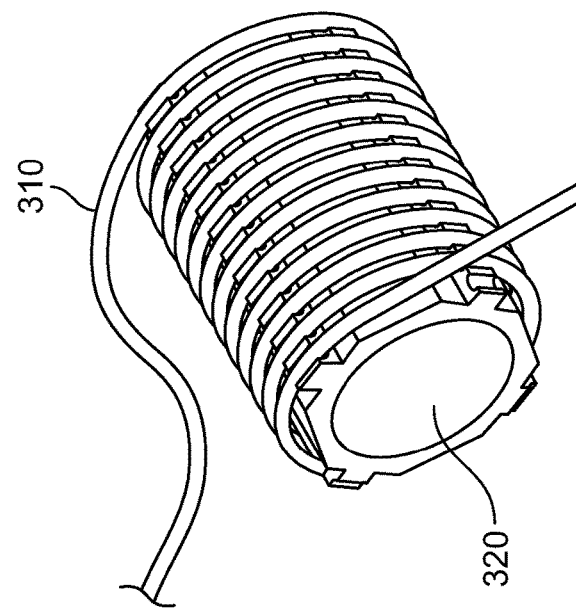
FIG. 6B
FIG. 7
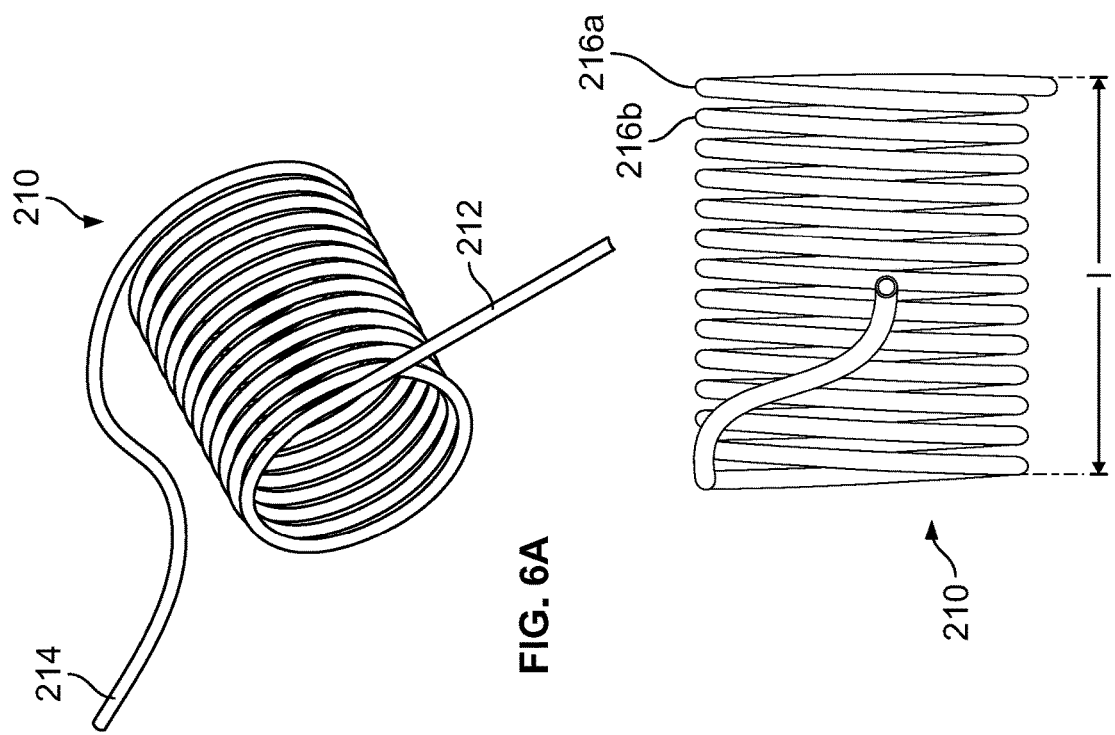
FIG. 6C

VAPOR ABLATION HANDPIECE

CROSS-REFERENCE TO RELATED APPLICATIONS

This application claims priority to Provisional Patent Application No. 62/598,138, filed Dec. 13, 2017 and entitled "VAPOR ABLATION HANDPIECE."

BACKGROUND OF THE INVENTION

The present invention is directed to tissue ablation by directing a condensable vapor at the tissue, and more particularly, to a handpiece for generating and controlling the condensable vapor to ablate the tissue.

Bronchoscopic vapor ablation is a minimally invasive medical procedure for treating various pulmonary diseases such as emphysema. Bronchoscopic vapor ablation can be applied to effectively reduce the volume of diseased lung tissue in a patient's lung, otherwise known as lung volume reduction surgery (LVRS). LVRS has been shown to improve patient pulmonary function in certain classes of patients.

In a bronchoscopic vapor ablation procedure, a bronchoscope is advanced into the lung of a patient to observe the target anatomy and to provide access to the target anatomy via a working lumen. Next, a vapor delivery catheter is advanced through the bronchoscope to the diseased lung segment. Vapor is applied to the target tissue through the catheter, heating the target tissue. Ablating the tissue serves to reduce the volume of the diseased tissue, allowing healthier tissue to perform the necessary pulmonary function.

Vapor ablation, however, is not without challenges. A liquid must be delivered to a vapor generator, the liquid is transformed to vapor, and the newly created vapor is transported to the catheter. The vapor is then carried through the catheter to the tissue. Heat loss can arise anywhere along the flow path. Perhaps worse, delivering too much vapor places the patient at risk for collateral damage can occur to healthy portions of the lung.

A number of patents describe systems for supplying a vapor to ablate a target tissue. U.S. Pat. No. 7,913,698 to Barry et al., e.g., describes methods and devices for affecting lung volume reduction, preferably for achieving acute or immediate lung volume reduction following treatment. The lung volume reduction is effected by delivering a condensable vapor at a temperature above body temperature to the desired regions of the patient's lung to damage tissue therein. Blood flow and air flow to the damaged tissue region is essentially terminated, rendering the target region non-functional. See also, U.S. Pat. No. 8,585,645 to Barry et al.

Although the above mentioned patents describe fine systems and methods for generating and delivering the vapor, the vapor is created by a generator remote to the catheter. A shortcoming of generating the vapor remote to the catheter is that heat loss may occur along the vapor flow path between the generator and catheter. This is undesirable.

Accordingly, there is still a need for improved vapor ablation that effectively generates, controls and delivers vapor to tissue while minimizing heat loss.

SUMMARY OF THE INVENTION

A vapor ablation handpiece for assisting a physician perform vapor ablation with a vapor ablation catheter includes a vapor generating element arranged in a coil shape. A mandrel seated in the body of the handpiece affixes the vapor generating element in the coiled arrangement. A voltage difference is supplied across the length of the vapor generating element when activated, causing the vapor generating element to heat liquid therein converting the liquid to a condensable vapor. The condensable vapor is delivered to a target tissue through the catheter.

In embodiments, the vapor generating element is an electrically conducting tube having a plurality of coil turns and the turns are seated in receptacles in the mandrel.

In embodiments, the vapor generating element has an orientation traverse to the barrel of the handpiece.

In embodiments, thermocouples are mounted or incorporated into locations along the flow path of the fluid. Temperature information is sent to a controller to monitor and adjust the voltage applied to the vapor generating element. The controller is programmed to adjust the temperature to maintain a steady flow of vapor through the catheter.

In embodiments, a vapor ablation system has a controller, a fluid supply to supply liquid, and a handpiece coupling the liquid to an elongate catheter. The handpiece includes a vapor generating element held in a coiled arrangement by a mandrel. The vapor generating element is operable with the controller to heat liquid flowing therethrough into vapor, and pass the vapor through the elongate catheter.

In embodiments, the fluid supply is a syringe.

In embodiments, the handpiece includes a cooling element to cool the vapor generating element. A fan is mounted in the body of the handpiece to aim air across the coil turns of the vapor generating element.

In embodiments, a method for ablating tissue with condensable vapor includes the following steps: providing an electrically conducting tube in a coiled arrangement; maintaining a gap between adjacent coil turns; transporting liquid through the electrically conducting tube; applying a voltage difference across the electrically conducting tube from a first end to a second end thereby converting the liquid to a condensable vapor; and delivering the condensable vapor to the tissue.

In embodiments, the method further includes the step of cooling the coil turns.

In embodiments, the maintaining step is performed with a mandrel.

In embodiments, the coil is interlocked with the mandrel by threading the coil and mandrel together.

In embodiments, the mandrel has a tubular body and is disposed within a lumen defined by the coiled arrangement of the electrically conducting tube.

In embodiments, the mandrel has a plurality of exteriorly disposed receptacles, and each receptacle is sized to engage a coil turn of the electrically conducting tube.

The description, objects and advantages of the present invention will become apparent from the detailed description to follow, together with the accompanying drawings.

BRIEF DESCRIPTION OF THE DRAWINGS

FIGS. 6A-6C are perspective, side, and front views respectively of a coil in accordance with an embodiment of the invention; and FIG. 7 is a perspective side view of the coil registered with the coil support in accordance with one embodiment of the invention.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Figure 1:
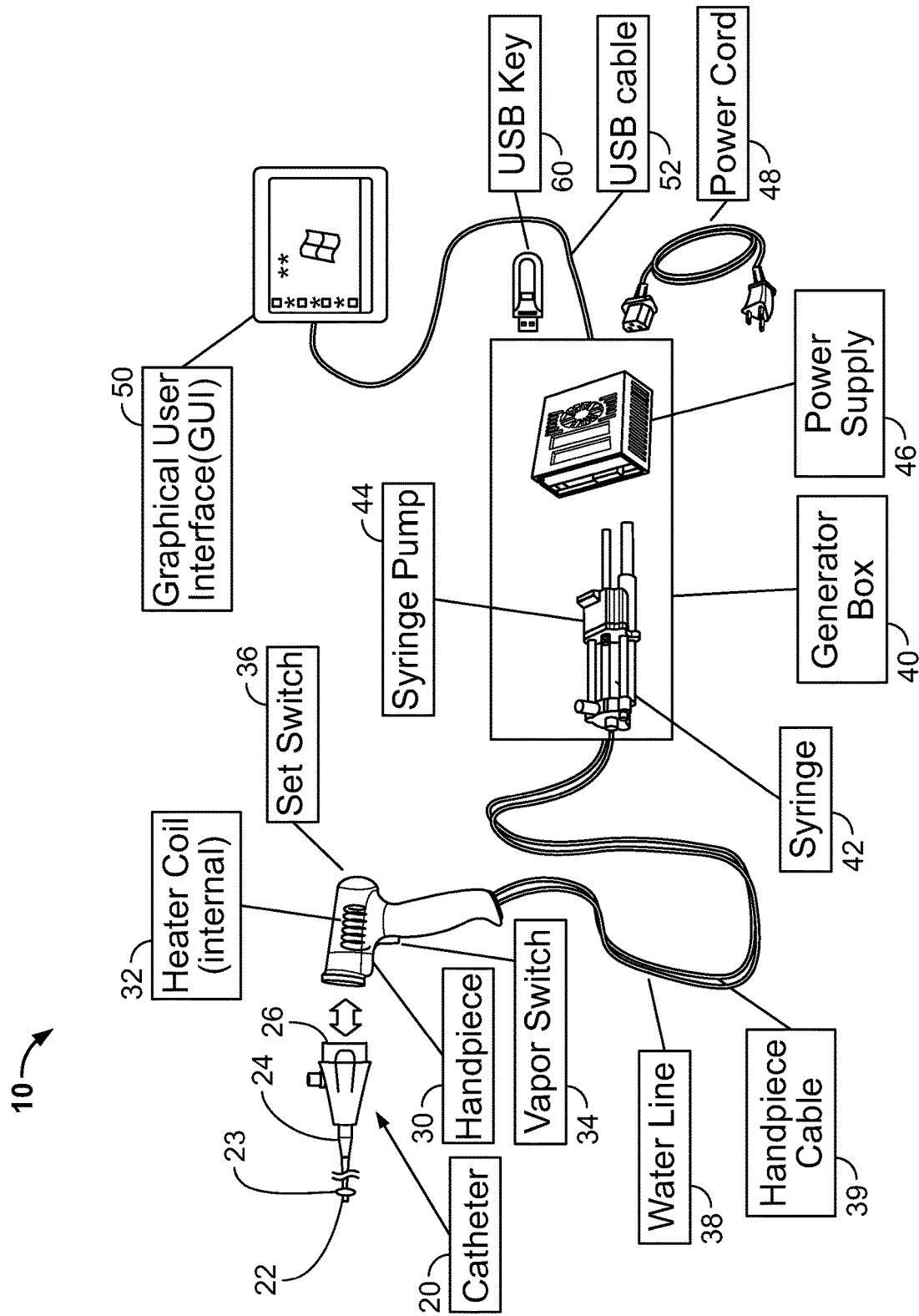
FIG. 1 is an illustration of a vapor ablation system.

FIG. 1 illustrates a vapor ablation system 10 which serves to generate and transport a condensable vapor to a target tissue, namely, lung or other tissue.

The vapor ablation system 10 is shown including a catheter 20 and handpiece 30 to which the catheter is removably joined.

The catheter 20 is shown comprising a distal end 22, an inflatable member 23, a flexible elongate shaft 24, and a proximal catheter hub 26 which may be joined to the handpiece 30. Examples of the catheter and components of the catheter are described in U.S. Pat. Nos. 7,913,698 and 8,585,645, both to Barry et al.

The handpiece 30 is shown in the shape of a pistol. The handpiece 30 includes a hollow coil 32 serving to convert liquid into a condensable vapor as it passes therethrough. The handpiece is shown with a vapor switch 34 and a set switch 36 which collectively serve to activate the vapor delivery.

In embodiments, the set switch 36 enables operation of the vapor switch 34 for a pre-set period of time (e.g., 10-20 seconds). After the set period of time, the vapor switch 34 is disabled for operation.

The handpiece is fluidly and electrically coupled to generator 40 via a water line 38 and electrical or control cable 39 respectively. An example of water line 38 is a flexible non-electrically conductive polymeric tube. Examples of a handpiece operation and various components therein are described in US Patent Publication No. 2016/0220297 to Kroon et al.

Generator 40 is shown housing a syringe 42, syringe pump 44, and power supply 46. The syringe and pump operate together to store and transport a liquid to the heater coil 32 of the handpiece 30 through the water line 38. Liquid may be sent to and delivered from handpiece continuously or in short pulses as desired. Generator 40 may also house various other components including processor(s) and storage components which are programmed or operable to carry out the methods described herein including actuating the pump to deliver a predetermined amount of liquid to the handpiece.

A graphical user interface (GUI) 50 (e.g., a tablet) is shown connected to the generator 40 via a cable 52. However, other interfaces may be employed including display and keyboard, smartphone, mouse, etc. The generator may be connected to remote GUIs and servers via the internet or other networks. Additionally, a USB key is shown which may include instructions thereon to activate the controller within certain parameters or conditions such as, for example, the requirement that the catheter has not been used previously. In embodiments, the system (via use of the USB key or otherwise) is adapted to prohibit use of the catheter after a pre-determined number of uses. Examples of generators and controller operation and components therein are described in U.S. Pat. Nos. 7,913,698 and 8,585,645, both to Barry et al.

Figure 2:
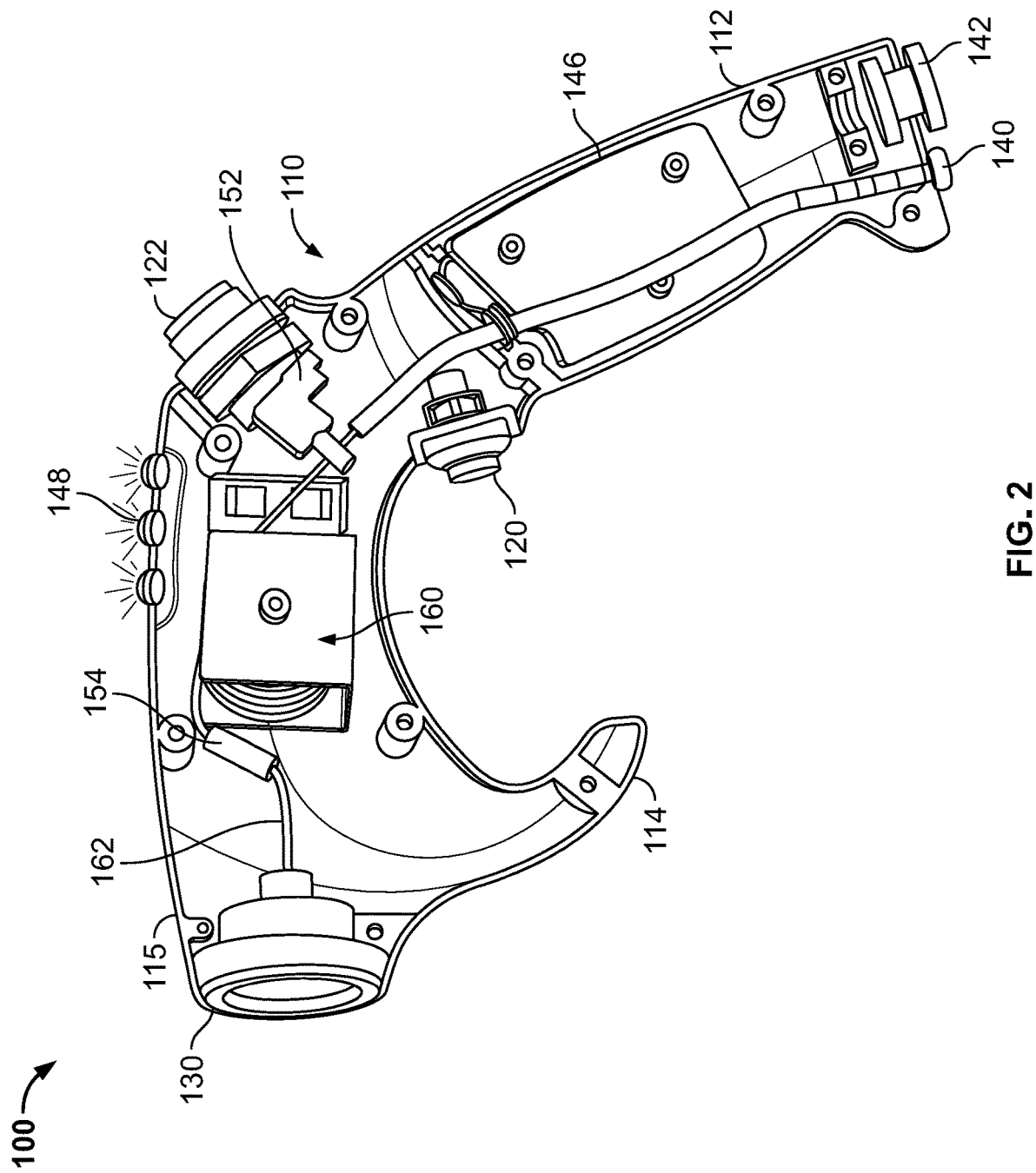
FIG. 2 is a side view of a handpiece of a vapor ablation system with a portion of the handpiece removed to show various components therein.

FIG. 2 illustrates another handpiece 100 sharing some of the features and functions with the handpiece shown in FIG. 1. Handpiece 100 has a pistol-shaped body 110 including a grip portion 112 and hook 114 for hanging the handpiece when not in use.

Similar to the handpiece described above in connection with FIG. 1, the handpiece 100 includes a vapor switch 120 and a set switch 122 which serve to collectively safely activate vapor delivery.

The handpiece 100 includes a female-type quick connect 130 to accept and register a proximal end of a vapor delivery catheter such as the catheter hub 26 described above.

The handpiece 100 is shown with a connector 140 for receiving liquid and the water line 38 described above. An exemplary connector 140 is a stainless-steel female Luer lock connector.

Adjacent the liquid line connector 140 is an opening 142 to receive a cable such as the control cable 39 described above. The opening 142 is shown in the form of a rubber grommet. Electrical conductors can extend through the opening 142 from the generator and provide signals and current to various components of the handpiece including, e.g., circuit board 146, light indicator array 148, first electrical terminus 152, and second electrical terminus 154. The wire conductors, however, have been removed from FIG. 2 in order to facilitate visibility and understanding of the other components in the handpiece discussed herein.

In embodiments, the handpiece 100 includes two PC boards: one board houses all the lights. The second board operates the thermocouples, buttons, and light board. Incorporating multiple PC boards into the handpiece is advantageous because the number of electrical wires traversing from the handpiece to the generator box is reduced.

Handpiece 100 is also shown having a discrete vapor generating element 160 for heating the liquid to vapor. The vapor generating element of FIG. 2 comprises tube made of an electrically conducting material and arranged in a coil configuration which is traverse to the barrel 115 of handpiece. The vapor generating element 160 is shown as a bare or sheath-less discrete element or component. It is shown commencing and terminating within the handle. The vapor generating element 160 may have a uniform wall thickness and electrical resistance along its length. A voltage difference is applied between the first electrical terminus 152 and the second electrical terminus 154 creating a current along the vapor generating element. The vapor generating element is heated due to resistance to the current. The liquid within the coil quickly turns to vapor.

One or more temperature sensors may be incorporated into the fluid path to measure temperature, and provide temperature information to the processor in the handpiece or controller of the vapor ablation system. The controller may adjust voltage to the vapor generating element to raise or lower the temperature. In embodiments, the vapor generating element is operable to avoid raising the temperature of the vapor above 150° C., and in some embodiments avoids raising the temperature of the vapor above about 115° C.

Figure 3:
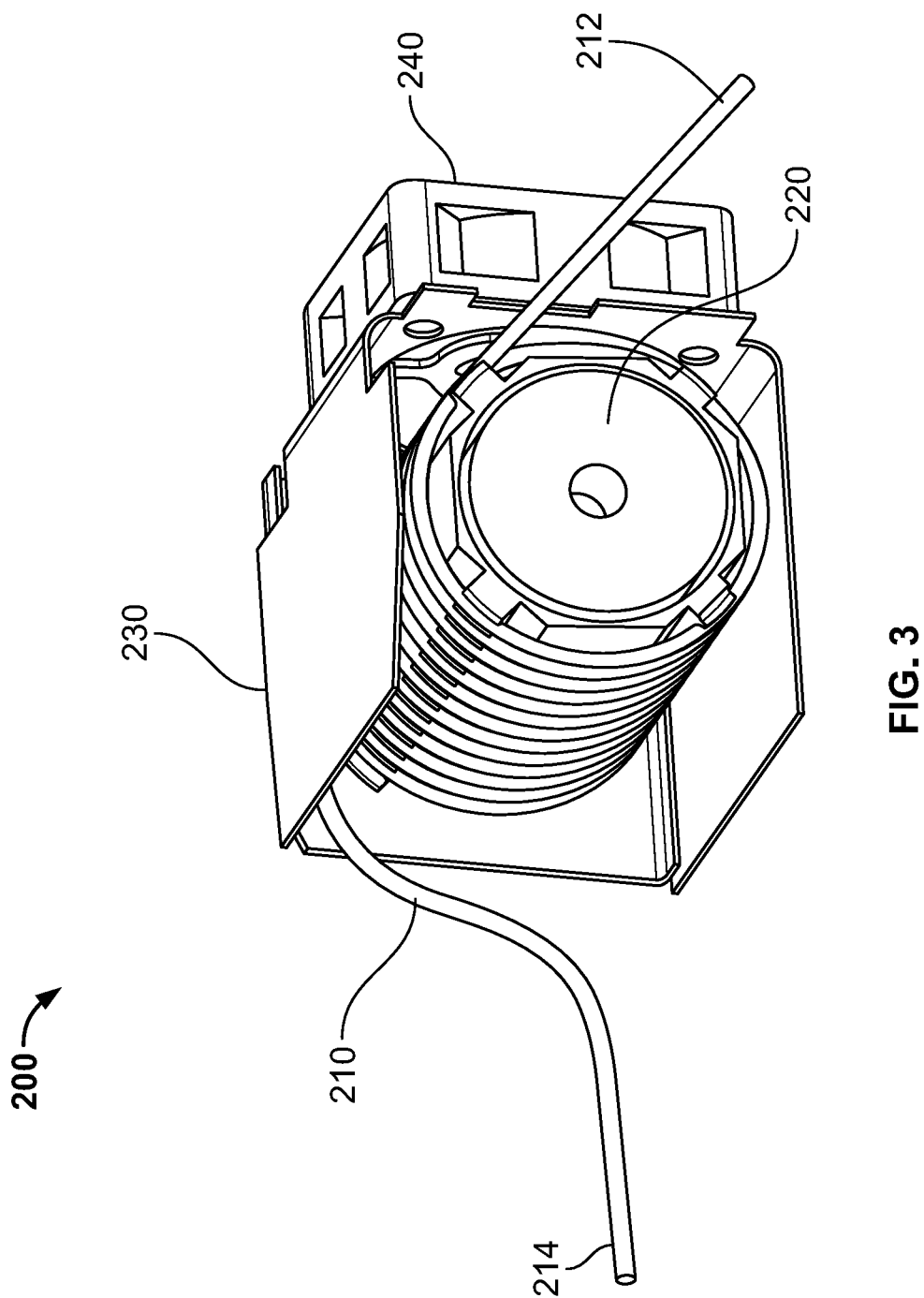
FIG. 3 is partial side perspective view of a coil assembly in accordance with one embodiment of the invention.

FIG. 3 is a partial view of an illustration of a heater coil assembly 200 including a vapor generating element 210, support 220, housing 230, and fan 240. As described herein, liquid enters the vapor generating element 210 at entry region 212 and is heated by the coil walls, turning to vapor. By the time the fluid reaches the exit region 214, the fluid is converted to vapor.

As shown in FIG. 3, and discussed further herein, the vapor generating element 210 is configured as a coil comprising a plurality of loops or turns. The coiled arrangement is held in place on a support 220.

A housing 230 and fan 240 are arranged to direct air across the vapor generating element 210 and support 220, serving to cool the assembly and prevent overheating of the handpiece.

Figure 4:
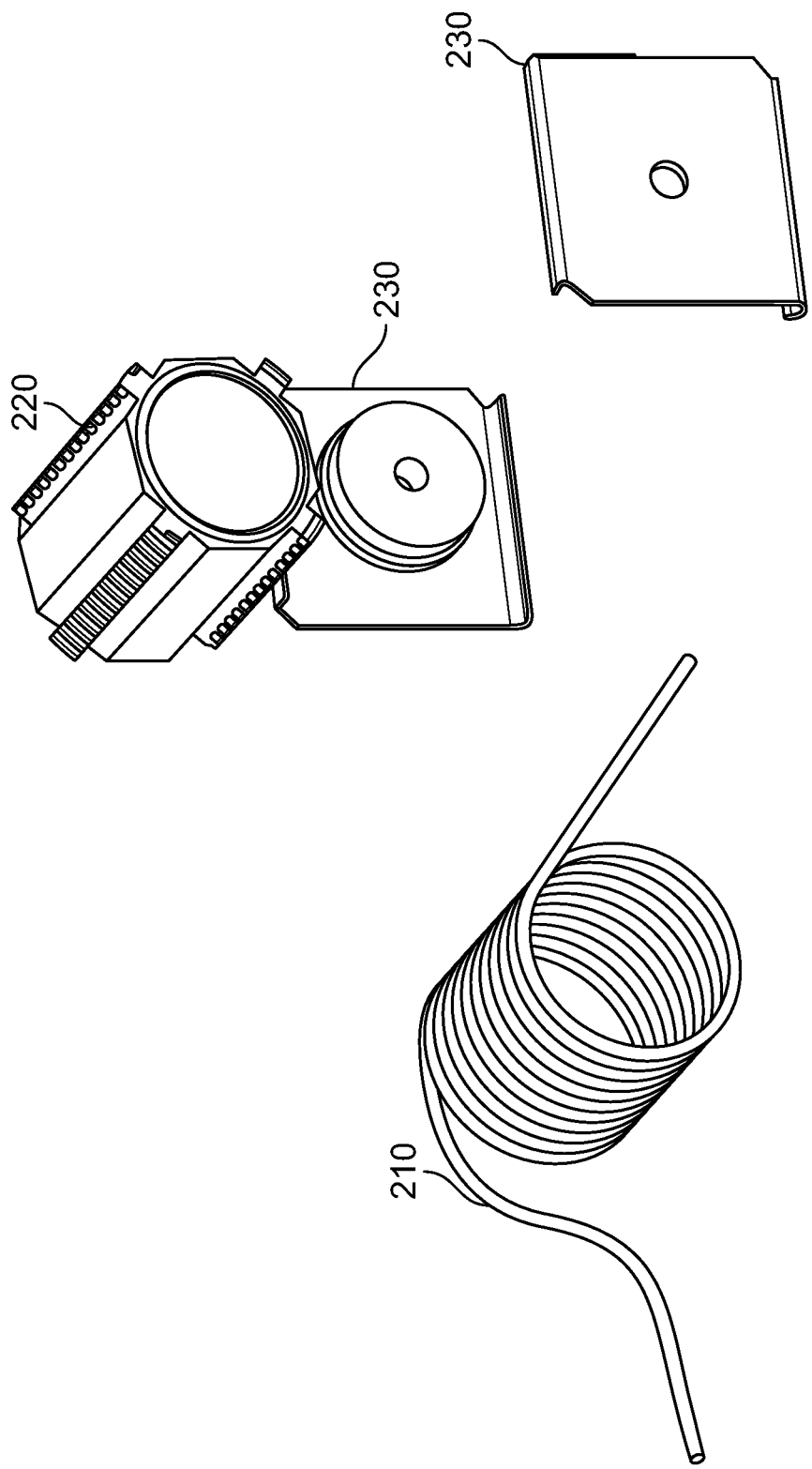
FIG. 4 is an exploded view of a coil assembly in accordance with one embodiment of the invention.

FIG. 4 is an exploded view of the coil 210, support 220, and housing walls 230.

Mandrel—Coil Support

FIGS. 5A-5D illustrate various engineering views of the coil support or mandrel 220 shown in FIG. 4. As described herein, the mandrel serves to hold the coil 210, maintain a spacing or gap between adjacent coil turns, and avoid acting as a heat sink to the extent possible.

The mandrel 220 is shown having a frame 230, a bridge 240, and a plurality of receptacles 242a, 242b, . . . . Each receptacle 240 is sized to accept and hold an individual coil turn, and maintain a gap (G) between adjacent coil turns. In embodiments, the gap (G) ranges from 0.03 to 0.1 inches, and more preferably is from 0.04 to 0.06 inches.

In embodiments, the mandrel has a length (L) ranging from 1-2 inches and more preferably from 1.5-1.75 inches, and in one embodiment is about 1.6 inches. In embodiments, the mandrel 220 has a diameter (D) ranging from 1 to 2 inches, and more preferably from about 1 to 1.25 inches.

As described above, the mandrel 220 is shown having a plurality of cups or receptacles 242a, 242b to hold individual coil turns of the tubular member 210. Particularly, the mandrel shown in FIGS. 5A-5C includes 14 receptacles to hold the 14 coil turns of the tube 210. However, the number of cups 242 in the bridge 240 may vary and be adjusted to properly hold or affix the coil 210 in its coiled arrangement.

Figure 5B:
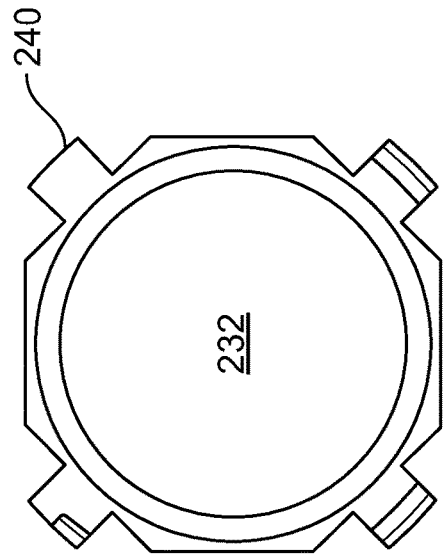
FIGS. 5A-5C are perspective, side, and front views respectively of a coil support in accordance with an embodiment of the invention.
Figure 5A:
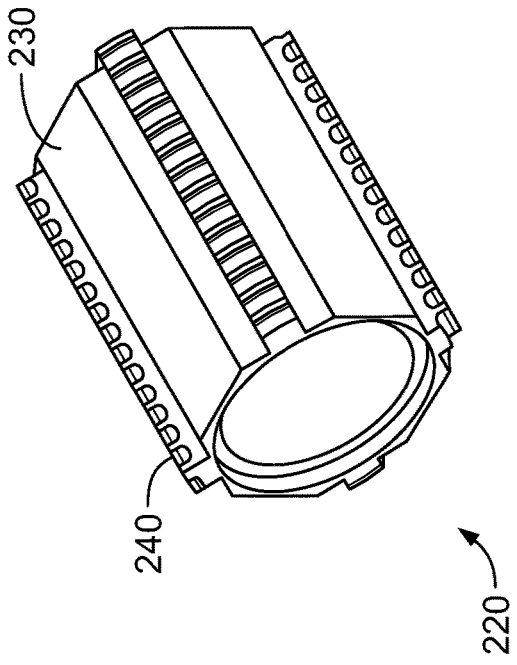
Figure 5D:
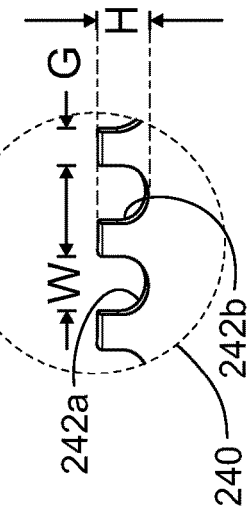
FIG. 5D is an enlarged view of a portion of coil support shown in FIGS. 5A-5C.
Figure 5C:
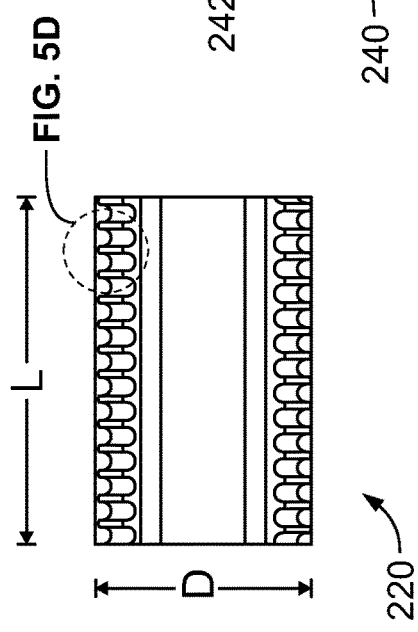

With reference to FIG. 5D, the receptacles 242a, 242b can have a height (H) ranging from 0.025 to 0.1 and preferably about 0.07 inches and a width (W) ranging from 0.025 to 0.1 and preferably about 0.08 inches. The receptacle or cup is also shown having a concave base to accept a coil turn of the tube 210 described herein.

The material of the mandrel may vary. An exemplary material for the mandrel is composite materials such as those sold under the trade name Accura Bluestone™ manufactured by 3D Systems Corporation (Rock Hill, S.C.), polycarbonates, or other high temperature plastics, and preferably a material that does not absorb heat from the coil tube 210.

Without intending to being bound to theory, the mandrel provides for separation of individual coils and limits the contact surface area between the metal tubing and the mandrel which results in less energy being absorbed to the mandrel. It is desirable to limit the energy absorbed to the mandrel.

Applicant recognized the above described phenomena. In embodiments of the invention, the contacting ratio (area in contact/area of entire tubing not in contact) is maintained to a range of 5 to 30%, and more preferably from 5 to 15%, and most preferably to less than or equal to 10%.

Additionally, the coil support 220 provides separation (namely, gaps) between individual coils. The spacing between the coil turns prevents the touching/shorting with each other to maintain the correct electrical properties when a voltage difference is applied along the length of the coil.

Vapor Generating Element—Coil

FIGS. 6A-6C show a tube (e.g., a steel hypotube) arranged in a coil 210. The coiled arrangement 210 includes a plurality of individual coil turns 216a, 216b, etc. In embodiments, the number of coil turns range from 10-20 turns. As fluid is transported through the coil, and a voltage difference is applied across the tube, the coil is heated to a temperature sufficient to vaporize the fluid therein. Without intending to being bound to theory, it is desirable to incorporate more coil turns into the tubular member to increase the heat transferred to the liquid in view of the limited volume/spacing within the handpiece.

In embodiments, the overall diameter (φ) of the coiled arrangement 210 ranges from 1 to 1.5 inches and preferably ranges from about 1 to 1.2 inches. Spacing between the coil turns can be maintained by the mandrel receptacles or cups 242 described above. In embodiments, the axial length of the coil is adapted to allow the coil to fit within the barrel and traverse to the barrel axis. In embodiments, the axial length (l) of coil is about the same as the mandrel, or about 1.5 to 1.75 inches.

The coiled arrangement 210 can be formed by winding a tubular member into the coiled arrangement. The tubular member includes a lumen to transport the fluid therethrough, and is made of an electrically conductive material. An exemplary material for the tubular member is 316L Stainless Steel welded and drawn tubing—passivated with an OD in the range from 0.05 to 0.1, and preferably about 0.072 inches; and an ID in the range from 0.03 to 0.1, and preferably about 0.06 inches.

The path length for the liquid or fluid to travel from the coil entrance 212 to the coil exit 214 ranges from 1000-2000 mm, and in embodiments ranges from about 1000-1300 mm. Increasing the path length serves to transfer more heat to the liquid, and to vaporize the liquid as the liquid flows therethrough. As stated herein, in embodiments, the path length is increased by incorporating more turns into the tubular member.

In embodiments, the vapor path is adapted to withstand high pressure without leaking such as a pressure of 125 psi when heated to 250° C. Exemplary materials for the vapor path 162 include those described above in connection with the coil and which can withstand the desirable operating pressures.

FIG. 7 is a perspective side view of another coil 310 registered with the coil support 320 in accordance with one embodiment of the invention. The assembly is heat efficient in the sense that a substantial amount of heat may be applied to the liquid in a relatively small space within the handpiece. Also, the mandrel 320 holds the coil in place, traverse to the barrel, and maintains spacing between each turn so the coil does not electrically short.

In embodiments, the coil 310 is interlocked with the mandrel 320 by screwing the coil onto the mandrel (or vice versa) just as one would interlock a screw and nut.

Other modifications and variations can be made to the disclosed embodiments without departing from the subject invention.

For example, in embodiments, both the set and vapor switches are not required and only one vapor or trigger switch is present to commence the vapor delivery.

Additionally, in embodiments, the vapor generating element is maintained parallel or in axial alignment with the barrel of the handpiece.

In embodiments, a vapor ablation system comprises a controller; a fluid supply to supply liquid; a handpiece comprising a vapor generating element held in a coiled arrangement by a mandrel, the vapor generating element operable with the controller to heat the liquid flowing therethrough into vapor; and an elongate catheter. In embodiments, the fluid supply may be a syringe.

In embodiments, the vapor generating element comprises an electrically conducting tube and a plurality of coil turns.

In embodiments, the vapor ablation system further comprises a mandrel, and the mandrel has a plurality of exteriorly disposed receptacles, and each receptacle sized to engage a coil turn of the electrically conducting tube.

In embodiments, the electrically conducting tube and mandrel are interlockingly arranged such that a contacting ratio of an area of the tube making contact with the mandrel is less than or equal to 10%.

In embodiments, the tube has a path length greater or equal to 1000 mm. In embodiments, the tube is fully contained within the body of the handpiece.

In embodiments, a method for ablating tissue with condensable vapor comprises the following steps: providing an electrically conducting tube in a coiled arrangement; maintaining a gap between adjacent coil turns; transporting liquid through the tube; applying a voltage difference across the tube from a first end to a second end thereby converting the liquid to a condensable vapor; and delivering the condensable vapor to the tissue.

In embodiments, the method further comprises cooling the coil turns.

In embodiments, the maintaining step is performed with a mandrel.

In embodiments, the coil is interlocked with the mandrel by threading the coil and mandrel together.

We claim:

1. A vapor ablation handpiece for assisting a physician perform vapor ablation with a vapor ablation catheter, the handpiece comprising:
   a body comprising a proximal end and a distal end, wherein the distal end is adapted to engage a proximal section of the vapor ablation catheter;
   a liquid input port for receiving a liquid;
   an electrically conducting tube comprising a first end, a second end, and having a coiled arrangement comprising a plurality of coil turns;
   a mandrel attached to the body supporting the electrically conducting tube in the coiled arrangement; and
   a first electrical conductor in electrical communication with the first end of the electrically conducting tube, and a second electrical conductor in electrical communication with the second end of the electrically conducting tube for supplying a voltage difference across the electrically conducting tube when activated and causing the electrically conducting tube to heat liquid therein converting the liquid to vapor by electrical resistance, and
   wherein the electrically conducting tube and mandrel are interlockingly arranged such that a contacting ratio of an area of the electrically conducting tube making contact with the mandrel is less than or equal to 10%.

2. The vapor ablation handpiece of claim 1 wherein the mandrel maintains a gap between adjacent coil turns.

3. The vapor ablation handpiece of claim 2 wherein each said gap between the coil turns is at least 0.05 inches.

4. The vapor ablation handpiece of claim 1 wherein an axial length of the electrically conducting tube from the first end to the second end is at least 1 inch.

5. The vapor ablation handpiece of claim 1 wherein the electrically conducting tube has an inner diameter in the range from 0.05 to 0.1 inches.

6. The vapor ablation handpiece of claim 1 wherein the coiled arrangement has a diameter in the range from 1 to 1.5 inches.

7. The vapor ablation handpiece of claim 1 further comprising a switch for controlling a function of the vapor ablation catheter when the vapor ablation catheter is connected to the vapor ablation handpiece.

8. The vapor ablation handpiece of claim 7 wherein the switch activates the vapor catheter to deliver vapor continuously.

9. The vapor ablation handpiece of claim 1 further comprising at least one light device to indicate status of the handpiece.

10. The vapor ablation handpiece of claim 1 wherein the body is pistol-shaped.

11. The vapor ablation handpiece of claim 10 further comprising a hook-shaped projection for hanging the handpiece.

12. The vapor ablation handpiece of claim 1, wherein the body of the handpiece defines a first axis that extends in a first direction, and wherein the coiled arrangement defines a second axis, wherein the second axis is traverse relative to the first axis of the body of the handpiece.

13. The vapor ablation handpiece of claim 1 further comprising a fan aimed at the electrically conducting tube.

14. The vapor ablation handpiece of claim 1 further comprising at least one thermocouple.

15. The vapor ablation handpiece of claim 1 wherein the electrically conducting tube is a steel.

16. The vapor ablation handpiece of claim 1 further comprising a flexible electrical cable extending from the proximal end of the handle, and said cable comprising a connector for connecting to a vapor ablation controller.

17. The vapor ablation handpiece of claim 1 wherein the mandrel comprises a frame, and a plurality of receptacles, and wherein each receptacle is sized to accept an individual coil turn and hold the individual coil turn in place and to maintain a gap between adjacent coil turns.

18. The vapor ablation handpiece of claim 17 wherein the coiled arrangement includes at least 15 coil turns.

19. A vapor ablation handpiece for assisting a physician perform vapor ablation with a vapor ablation catheter, the handpiece comprising:
  a body comprising a proximal end and a distal end, wherein the distal end is adapted to engage a proximal section of the vapor ablation catheter;
  a liquid input port for receiving a liquid;
  a vapor generating element comprising a first end, a second end, and an electrically conducting tube in a coiled arrangement comprising a plurality of coil turns;
  a mandrel attached to the body supporting the electrically conducting tube in the coiled arrangement; and
  a first electrical conductor in electrical communication with the first end of the vapor generating element, and a second electrical conductor in electrical communication with the second end of the vapor generating element for supplying a voltage difference across the vapor generating element when activated and causing the vapor generating element to heat liquid therein converting the liquid to vapor, and
  wherein the electrically conducting tube and mandrel are interlockingly arranged such that a contacting ratio of an area of the electrically conducting tube making contact with the mandrel is less than or equal to 10%.

20. A method for ablating tissue with condensable vapor comprising:
  providing a handpiece, the handpiece comprising a mandrel and an electrically conducting tube supported by the mandrel in a coiled arrangement within the handpiece;
  maintaining a gap between adjacent coil turns;
  transporting liquid through the electrically conducting tube;
  electrically resistively heating the electrically conducting tube by applying a voltage difference across the electrically conducting tube from a first end to a second end within the handpiece, thereby converting the liquid to a condensable vapor; and
  delivering the condensable vapor to the tissue, and
  wherein the step of maintaining is performed by controlling a contacting ratio of an area of the electrically conducting tube making contact with the mandrel to less than or equal to 10%.

* * * * *